(12) United States Patent  (10) Patent No.: US 9,216,071 B2
Di Cosola  (45) Date of Patent: Dec. 22, 2015

(54) DENTAL ANCHOR IMPLANT DEVICE

(71) Applicant: Michelangelo Di Cosola, Bloomingdale, IL (US)

(72) Inventor: Michelangelo Di Cosola, Bloomingdale, IL (US)

( * ) Notice: Subject to any disclaimer, the term of this patent is extended or adjusted under 35 U.S.C. 154(b) by 31 days.

(21) Appl. No.: 14/219,216

(22) Filed: Mar. 19, 2014

(65) Prior Publication Data

US 2015/0265382 A1  Sep. 24, 2015

(51) Int. Cl.
*A61C 13/08* (2006.01)
*A61C 13/24* (2006.01)
*A61C 13/103* (2006.01)
*A61C 13/271* (2006.01)

(52) U.S. Cl.
CPC ............ *A61C 13/245* (2013.01); *A61C 13/08* (2013.01); *A61C 13/1009* (2013.01); *A61C 13/26* (2013.01)

(58) Field of Classification Search
CPC ............ A61C 8/0031; A61C 13/1009; A61C 13/245; A61C 13/26; A61C 13/08
See application file for complete search history.

(56) References Cited

U.S. PATENT DOCUMENTS

| 1,312,141 | A | * | 8/1919 | Slack | 433/211 |
| 4,180,910 | A |  | 1/1980 | Straumann et al. | |
| 4,379,694 | A | * | 4/1983 | Riess | 433/201.1 |
| 4,702,697 | A | * | 10/1987 | Linkow | 433/173 |
| 4,828,492 | A |  | 5/1989 | Agnone | |
| 4,995,811 | A |  | 2/1991 | Cecconi | |
| 5,133,662 | A | * | 7/1992 | Metcalfe | 433/169 |
| 5,906,489 | A | * | 5/1999 | Khazzam et al. | 433/176 |
| 6,287,118 | B1 | * | 9/2001 | Naganuma et al. | 433/176 |
| D487,314 | S |  | 3/2004 | Culp et al. | |
| D494,275 | S |  | 8/2004 | Whitehead | |
| 6,863,531 | B2 |  | 3/2005 | Kensuke et al. | |
| 2006/0154205 | A1 | * | 7/2006 | Reggie | 433/173 |
| 2007/0264612 | A1 |  | 11/2007 | Mount | |
| 2010/0112522 | A1 | * | 5/2010 | Kwon | 433/174 |

* cited by examiner

*Primary Examiner* — Ralph Lewis

(57) ABSTRACT

A dental anchor implant device anchors false teeth securely within a user's mouth. The device includes a base having a convex upper surface and a concave lower surface wherein the base is configured for positioning on and coupling to a top of a jawbone. An anchor is coupled to and extends upwardly from the upper surface of the base. A post extends upwardly from a top surface of the anchor. A tooth has a socket extending into a bottom surface of the tooth. The post is positionable in the socket wherein the post inhibits lateral movement of the bottom surface of the tooth relative to the top surface of the anchor. The bottom surface of the tooth is substantially complementary to the top surface of the anchor.

11 Claims, 4 Drawing Sheets

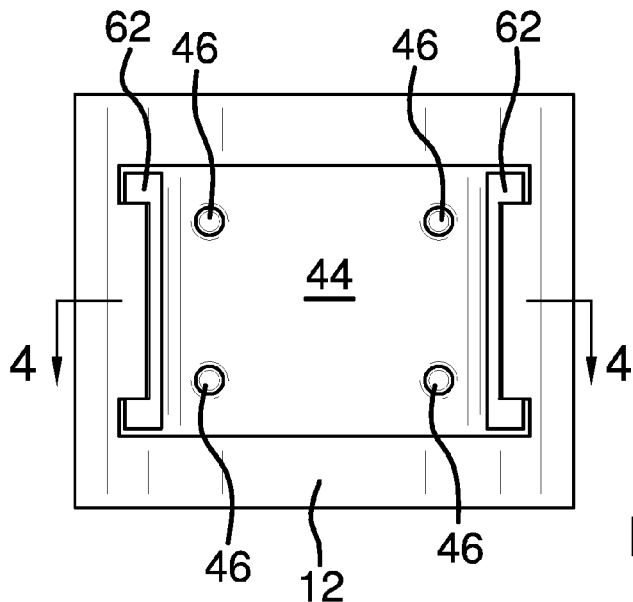
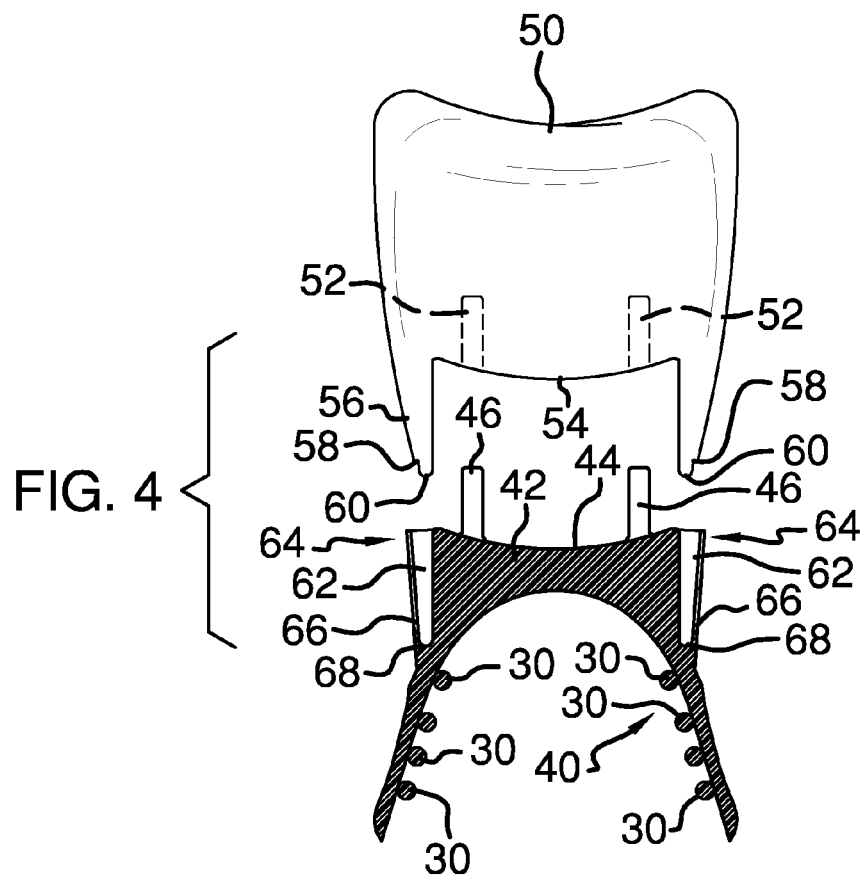

DENTAL ANCHOR IMPLANT DEVICE

BACKGROUND OF THE DISCLOSURE

Field of the Disclosure

The disclosure relates to implant devices and more particularly pertains to a new implant device for anchoring false teeth securely within a user's mouth.

SUMMARY OF THE DISCLOSURE

An embodiment of the disclosure meets the needs presented above by generally comprising a base having a convex upper surface and a concave lower surface wherein the base is configured for positioning on and coupling to a top of a jawbone. An anchor is coupled to and extends upwardly from the upper surface of the base. A post extends upwardly from a top surface of the anchor. A tooth has a socket extending into a bottom surface of the tooth. The post is positionable in the socket wherein the post inhibits lateral movement of the bottom surface of the tooth relative to the top surface of the anchor. The bottom surface of the tooth is substantially complementary to the top surface of the anchor.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF THE DRAWINGS

The disclosure will be better understood and objects other than those set forth above will become apparent when consideration is given to the following detailed description thereof. Such description makes reference to the annexed drawings wherein:

FIG. 3 is a top view of a single tooth embodiment of the disclosure.

FIG. 4 is a cross-sectional view of an embodiment of the disclosure taken along line 4-4 of FIG. 3.

DESCRIPTION OF THE PREFERRED EMBODIMENT

Figure 1:
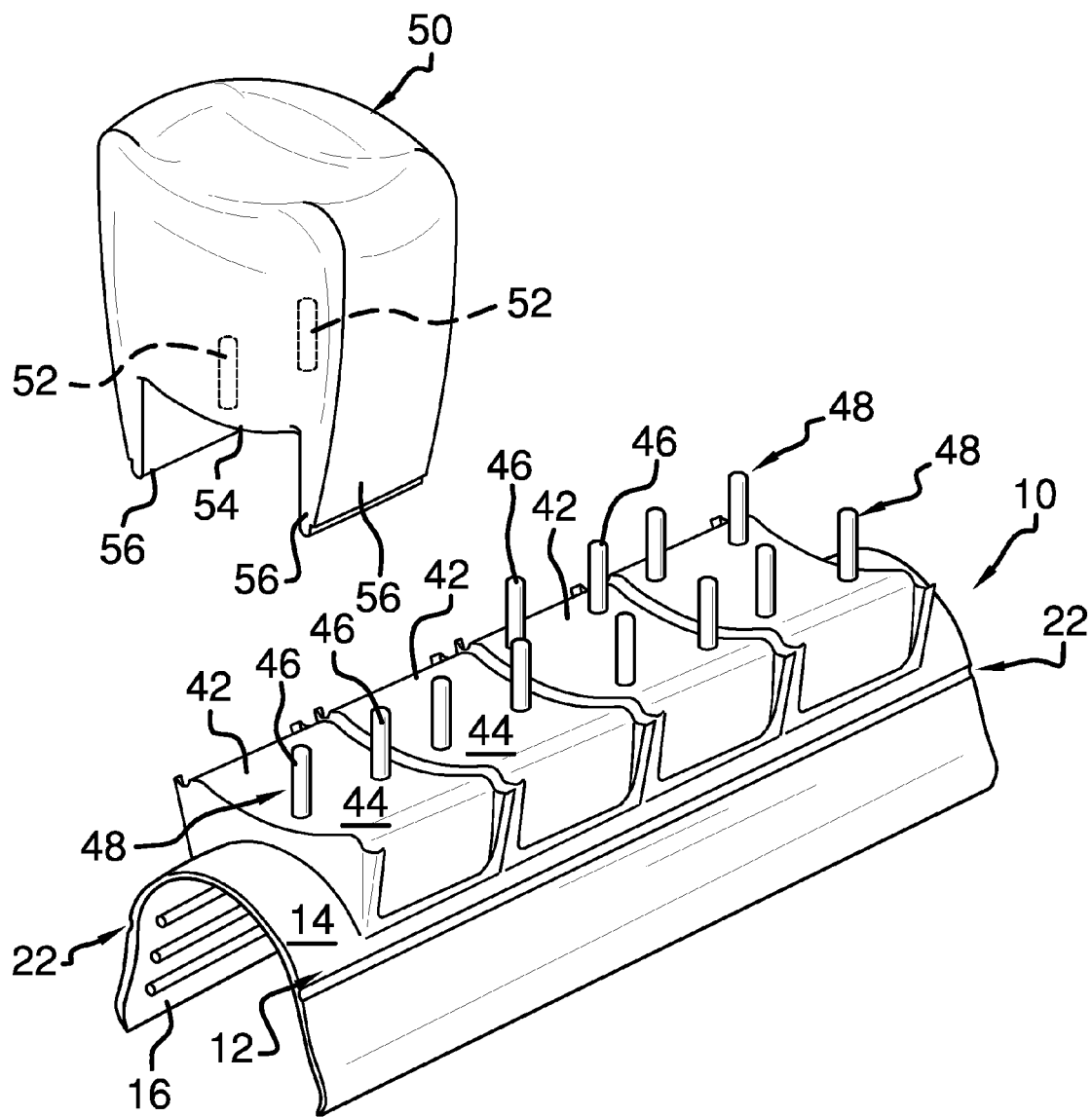
FIG. 1 is a top front side perspective view of a dental anchor implant device according to an embodiment of the disclosure.
Figure 2:
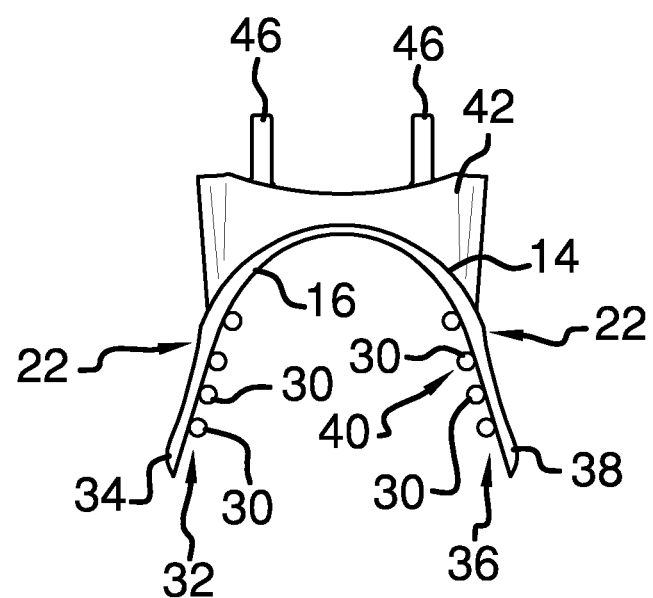
FIG. 2 is a front view of an embodiment of the disclosure.
Figure 5:
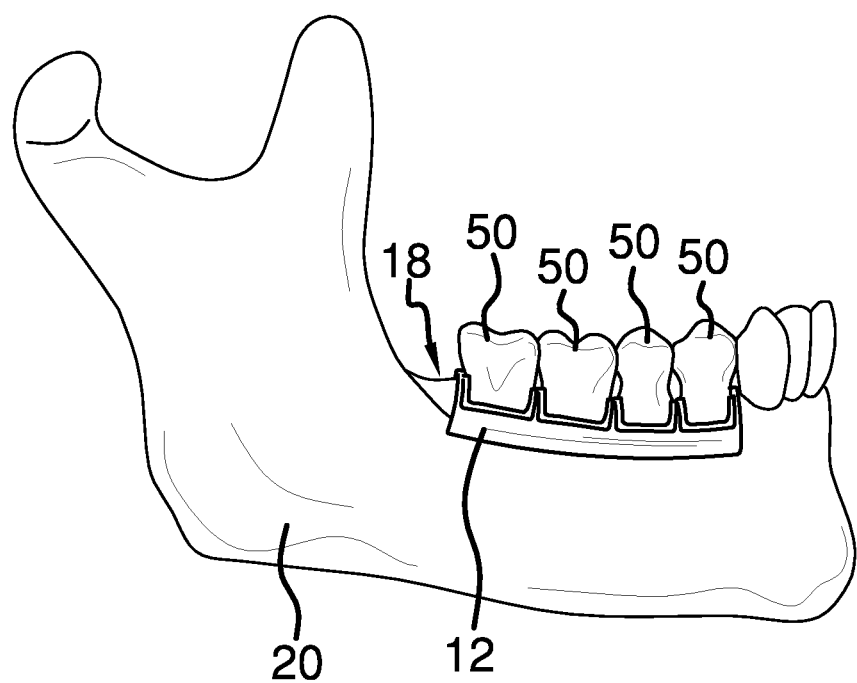
FIG. 5 is a side view of an embodiment of the disclosure coupled to a jawbone.

With reference now to the drawings, and in particular to FIGS. 1 through 5 thereof, a new implant device embodying the principles and concepts of an embodiment of the disclosure and generally designated by the reference numeral 10 will be described.

As best illustrated in FIGS. 1 through 5, the dental anchor implant device 10 generally comprises an elongated base 12 having a convex upper surface 14 and a concave lower surface 16 wherein the base 12 is configured for positioning on and coupling to a top 18 of a jawbone 20. The upper surface 14 has a pair of lengthwise depressions 22 extending between a first end 24 of the base 12 and a second end 26 of the base 12 wherein the upper surface 14 is configured for facilitating retention of a user's gums 28 over the upper surface 14 when the base 12 is coupled to the jawbone 20. Each of a plurality of ridges 30 extends from the lower surface 16 of the base 12. Each of the ridges 30 is parallel to a longitudinal axis of the base 12. The ridges 30 are arranged into a first array 32 positioned on a first lateral side 34 of the lower surface 16 of the base 12 and a second array 36 positioned on a second lateral side 38 of the lower surface 16 of the base 12. Each of the ridges 30 is substantially cylindrical having a circular transverse cross-sectional shape 40.

Each of a plurality of anchors 42 is coupled to and extends upwardly from the upper surface 14 of the base 12. Each anchor 42 has a respective top surface 44. Each of a plurality of posts 46 extends upwardly from the top surface 44 of an associated one of the anchors 42. The posts 46 extend from each anchor 42 parallel and spaced extending upwardly from the top surface 44 of the associated anchor 42. The posts 46 are arranged into associated pairs 48. Each anchor 42 may have one or two associated pairs 48 with a single pair being used for teeth near a front of the mouth and two pairs being used for molars near a rear of the mouth. Each associated pair 48 may be laterally spaced and aligned along a longitudinal axis of the base 12 or laterally spaced and aligned parallel to the longitudinal axis of the base 12.

Each of a plurality of teeth 50 is couplable to an associated anchor 42. Each tooth 50 is a replacement for a natural tooth no longer present in the mouth and may be produced in a conventional manner. Each tooth 50 has a plurality of sockets 52 extending into a bottom surface 54 of the tooth 50. Each post 46 is positionable in an associated one of the sockets 52 wherein the posts 46 inhibit lateral movement of the bottom surface 54 relative to the top surface 44 of the associated anchor 42. The bottom surface 54 of each tooth 50 is substantially complementary to the top surface 44 of the associated anchor 42 wherein the bottom surface 54 of the tooth 50 abuts the top surface 44 of the associated anchor 42 when the tooth 50 is positioned on the associated anchor 42.

A respective pair of lateral walls 56 extends downwardly from each tooth 50. Each lateral wall 56 has a respective shoulder 58 positioned proximate a terminal bottom end 60 of the lateral wall 56. A respective pair of slots 62 extends downwardly from the top surface 44 of an associated one of the anchors 42. Each slot 62 is positioned on an associated side 64 of the associated anchor 42. Each lateral wall 56 is received in an associated one of the slots 62 when the tooth 50 is positioned on the associated anchor 42. Each shoulder 58 abuts a base edge 66 positioned proximate a bottom 68 of a respective one of the slots 62. Thus, each tooth 50 is seated on the associated anchor 42 securely and may be affixed using adhesive or another conventional fastener.

The base 12, anchors 42, and posts 46 are integral to each other and may be constructed of titanium or the like suitable for dental implants.

In use, the base 12 is surgically implanted onto the jawbone 20. The base 12 may have one of more anchors 42 as needed for a particular patient. Teeth 50 are constructed and sized appropriately for the particular patient and secured to the base 12. The gums 28 would be extended over a bottom portion of each tooth 50 and stitched together between the teeth 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A dental anchor implant device comprising:
   a base having a convex upper surface and a concave lower surface wherein said base is configured for positioning on and coupling to a top of a jawbone;
   an anchor coupled to and extending upwardly from said upper surface of said base, said anchor having a top surface;
   a post extending upwardly from said top surface of said anchor;
   a tooth, said tooth having a socket extending into a bottom surface of said tooth, said post being positionable in said socket wherein said post inhibits lateral movement of said bottom surface relative to said top surface of said anchor, said bottom surface of said tooth being substantially complementary to said top surface of said anchor wherein said bottom surface of said tooth abuts said top surface of said anchor when said tooth is positioned on said anchor;
   a pair of lateral wall extending downwardly from said tooth; and
   a pair of slots, each of said slots extending downwardly from said top surface of said anchor on an associated side of said anchor, each said lateral wall being received in an associated one of said slots when said tooth is positioned on said anchor.

2. The device of claim 1, further comprising a plurality of ridges extending from said lower surface of said base.

3. The device of claim 2, further comprising each of said ridges being parallel to a longitudinal axis of said base.

4. The device of claim 3, further comprising said ridges being arranged into a first array positioned on a first lateral side of said lower surface of said base and a second array positioned on a second lateral side of said lower surface of said base.

5. The device of claim 2, further comprising each of said ridges being substantially cylindrical having a circular transverse cross-sectional shape.

6. The device of claim 1, further comprising said post being one of a plurality of posts, said posts being parallel and spaced extending upwardly from said top surface of said anchor.

7. The device of claim 6, further comprising said posts being arranged into associated pairs, each said associated pair being laterally aligned along a longitudinal axis of said base.

8. The device of claim 1, further comprising each lateral wall having a respective shoulder positioned proximate a terminal bottom end of said lateral wall, each said shoulder abutting a base edge positioned proximate a bottom of a respective one of said slots.

9. The device of claim 1, further comprising said upper surface having a pair of lengthwise depressions extending between a first end of said base and a second end of said base wherein said upper surface is configured for facilitating retention of a user's gums over said upper surface when said base is coupled to the user's jaw.

10. A dental anchor implant device comprising:
    a base having a convex upper surface and a concave lower surface wherein said base is configured for positioning on and coupling to a top of a jawbone, said upper surface having a pair of lengthwise depressions extending between a first end of said base and a second end of said base wherein said upper surface is configured for facilitating retention of a user's gums over said upper surface when said base is coupled to the user's jaw;
    a plurality of ridges extending from said lower surface of said base, each of said ridges being parallel to a longitudinal axis of said base, said ridges being arranged into a first array positioned on a first lateral side of said lower surface of said base and a second array positioned on a second lateral side of said lower surface of said base, each of said ridges being substantially cylindrical having a circular transverse cross-sectional shape;
    an anchor coupled to and extending upwardly from said upper surface of said base, said anchor having a top surface;
    a plurality of posts, each said post extending upwardly from said top surface of said anchor, said posts being parallel and spaced extending upwardly from said top surface of said anchor, said posts being arranged into associated pairs, each said associated pair being laterally aligned along a longitudinal axis of said base;
    a tooth, said tooth having a socket extending into a bottom surface of said tooth, said post being positionable in said socket wherein said post inhibits lateral movement of said bottom surface relative to said top surface of said anchor, said bottom surface of said tooth being substantially complementary to said top surface of said anchor wherein said bottom surface of said tooth abuts said top surface of said anchor when said tooth is positioned on said anchor;
    a pair of lateral wall extending downwardly from said tooth, each lateral wall having a respective shoulder positioned proximate a terminal bottom end of said lateral wall; and
    a pair of slots, each of said slots extending downwardly from said top surface of said anchor on an associated side of said anchor, each said lateral wall being received in an associated one of said slots when said tooth is positioned on said anchor, each said shoulder abutting a base edge positioned proximate a bottom of a respective one of said slots.

11. A dental anchor implant device comprising:
    a base having a convex upper surface and a concave lower surface wherein said base is configured for positioning on and coupling to a top of a jawbone, said upper surface having a pair of lengthwise depressions extending between a first end of said base and a second end of said base wherein said upper surface is configured for facilitating retention of a user's gums over said upper surface when said base is coupled to the user's jaw;
    a plurality of ridges extending from said lower surface of said base, each of said ridges being parallel to a longitudinal axis of said base, said ridges being arranged into a first array positioned on a first lateral side of said lower surface of said base and a second array positioned on a second lateral side of said lower surface of said base, each of said ridges being substantially cylindrical having a circular transverse cross-sectional shape;

a plurality of anchors, each said anchor being coupled to and extending upwardly from said upper surface of said base, each said anchor having a respective top surface;

a plurality of posts, each said post extending upwardly from said top surface of an associated one of said anchors, said posts extending from each said anchor being parallel and spaced extending upwardly from said top surface of said associated anchor, said posts being arranged into associated pairs, each said associated pair being laterally aligned along a longitudinal axis of said base;

a plurality of teeth, each said tooth being couplable to an associated said anchor, each said tooth having a plurality of sockets extending into a bottom surface of said tooth, each said post being positionable in an associated one of said sockets wherein said posts inhibits lateral movement of said bottom surface relative to said upper surface of said associated anchor, said bottom surface of each said tooth being substantially complementary to said top surface of said associated anchor wherein said bottom surface of said tooth abuts said top surface of said associated anchor when said tooth is positioned on said associated anchor;

a respective pair of lateral walls extending downwardly from each said tooth, each lateral wall having a respective shoulder positioned proximate a terminal bottom end of said lateral wall; and a respective pair of slots extending downwardly from said top surface of an associated said anchor, each said slot being positioned on an associated side of said associated anchor, each said lateral wall being received in an associated one of said slots when said tooth is positioned on said associated anchor, each said shoulder abutting a base edge positioned proximate a bottom of a respective one of said slots.

\* \* \* \* \*